US008859022B2

(12) United States Patent (10) Patent No.: US 8,859,022 B2
Hirayama et al. (45) Date of Patent: Oct. 14, 2014

(54) ANTIHYPERTENSIVE AGENTS

(75) Inventors: Masao Hirayama, Kashiwazaki (JP); Ryo Furuuchi, Kashiwazaki (JP); Tadayuki Yokoyama, Kashiwazaki (JP)

(73) Assignee: Bourbon Corporation, Kashiwazaki-shi (JP)

( * ) Notice: Subject to any disclaimer, the term of this patent is extended or adjusted under 35 U.S.C. 154(b) by 212 days.

(21) Appl. No.: 13/278,793

(22) Filed: Oct. 21, 2011

(65) Prior Publication Data

US 2013/0040005 A1 Feb. 14, 2013

(30) Foreign Application Priority Data

Aug. 10, 2011 (JP) ................................. 2011-175243

(51) Int. Cl.
| | | |
|---|---|---|
| A61K 36/73 | (2006.01) | |
| A23L 1/30 | (2006.01) | |
| A61K 31/353 | (2006.01) | |
| A23G 1/48 | (2006.01) | |
| A23G 3/48 | (2006.01) | |
| A23L 2/52 | (2006.01) | |

(52) U.S. Cl.
CPC ............. *A61K 31/353* (2013.01); *A23L 1/3002* (2013.01); *A23G 1/48* (2013.01); *A23G 3/48* (2013.01); *A23L 2/52* (2013.01); *A23V 2002/00* (2013.01)
USPC .......................................... 424/765; 424/776

(58) Field of Classification Search
None
See application file for complete search history.

(56) References Cited

U.S. PATENT DOCUMENTS

2007/0281044 A1 12/2007 Mueller et al.

FOREIGN PATENT DOCUMENTS

| CN | 1119076 A | 3/1996 |
|---|---|---|
| JP | A-2003-212783 | 7/2003 |
| JP | A-2008-156306 | 7/2008 |
| JP | A-2009-512638 | 3/2009 |
| JP | WO 2010/092941 A1 | 8/2010 |
| JP | A-2010-254590 | 11/2010 |
| KR | 10 2007 0080027 A | 8/2007 |
| WO | WO 2007/038685 A2 | 4/2007 |

OTHER PUBLICATIONS

Primary Prevention of Hypertension: Clinical and Public Health Advisory from the National High Blood Pressure Education Program. 2002. NIH Publication No. 02-5076.*
http://www.mayoclinic.com/health/blood-pressure/AN00391—accessed Oct. 13.*
Kool (Food Chemistry (Apr. 2010), vol. 119, pp. 1535-1543).*
Kubomura, "Boysenberry as a Functional Food Ingredient," *Journal of the Japan · Association for the Integrated Study of Dietary Habits*, 2005, pp. 44-49, vol. 16: No. 1 (with abstract).
Furuuchi et al., "Analysis of proanthocyanidins in Boysenberry juice and in vitro vasorelaxant effect," *Proceedings of the 64th Annual Meeting of Japan Society of Nutrition and Food Science*, 2010 (with partial translation).
Monagas et al., "Monomeric, Oligomeric, and Polymeric Flavan-3-ol Composition of Wines and Grapes from *Vitis vinifera* L. Cv. Graciano, Tempranillo, and Cabernet Sauvignon," *Journal of Agricultural and Food Chemistry*, 2003, p. 6475-6481 vol. 51.
Holt et al., "Procyanidin dimer B2 [epicatechin-(4β-8)-epicatechin] in human plasma after the consumption of a flavanol-rich cocoa," *Am. J. Clin. Nutr.*, 2002, p. 798-804, vol. 76.
Shoji et al., "Apple Procyanidin Oligomers Absorption in Rats after Oral Administration: Analysis of Procyanidins in Plasma Using the Porter Method and High-Performance Liquid Chromatography/Tandem Mass Spectrometry," *Journal of Agricultural and Food Chemistry*, 2006, p. 884-892, vol. 54.
Sera et al., "Bioavailability of procyanidin dimers and trimers and matrix food effects in vitro and in vivo models," *British Journal of Nutrition*, 2010, p. 944-952, vol. 103.
Furuuchi et al., "Identification and Quantification of Short Oligomeric Proanthocyanidins and Other Polyphenols in Boysenberry Seeds and Juice," *Journal of Agricultural and Food Chemistry*, 2011, p. 3738-3746, vol. 59.
Furuuchi et al., "Chronological Change in Blood Pressure in Spontaneously Hypertensive Rats (SHRs) by Single-Dose Administration of Boysenberry Seed Polyphenol," *Proceedings of the 65th Annual Meeting of Japan Society of Nutrition and Food Science*, Apr. 25, 2011 (with partial translation).
Parry et al., "Fatty acid composition and antioxidant properties of cold-pressed marionberry, boysenberry, red raspberry, and blueberry seed oils." *Journal of Agricultural and Food Chemistry*, 2005, pp. 566-573, vol. 53, United States.
Oct. 27, 2011 Office Action issued in New Zealand Patent Application No. 595951.
Feb. 12, 2013 Office Action issued in New Zealand Application No. 595951.
Ryo Furuuchi et al., Polyphenols Communications 2010, Montpellier—France, Aug. 24-27, 2010, vol. 2, pp. 378-379.
Kayoko Kawakami et al., "Major Water-Soluble Polyphenols, Proanthocyanidins, in Leaves of Persimmon (*Diospyros kaki*) and Their α-Amylase Inhibitory Activity," Department of Food Science, Niigata University of Pharmacy and Applied Life Sciences, Niigata 956-8603, Japan, Biosci. Biotechnol. Biochem, 74(7), pp. 1380-1385, 2010.

* cited by examiner

*Primary Examiner* — Susan Hoffman
(74) *Attorney, Agent, or Firm* — Oliff PLC

(57) ABSTRACT

The present invention relates to an antihypertensive agent including a boysenberry seed extract as an active ingredient. According to the invention, there can be provided an effective and highly safe antihypertensive agent having antihypertensive effect so that the agent can contribute to the prevention and amelioration of hypertension and having very little risk of side effects even in continuous intake, and a method for producing the antihypertensive agent at low cost and efficiently.

18 Claims, 6 Drawing Sheets

ANTIHYPERTENSIVE AGENTS

CROSS-REFERENCE TO RELATED APPLICATION

This application is based on and claims the benefit of priority from the preceding Japanese Patent Application No 2011-175243 (filed on Aug. 10, 2011), the entire contents of which are incorporated herein by reference.

BACKGROUND OF THE INVENTION

1. Field of the Invention

The present invention relates to an antihypertensive agent comprising a Boysenberry seed extract as an active ingredient, and to a method for producing the antihypertensive agent. The invention also relates to a food and beverage product composition and a pharmaceutical product composition, which include the antihypertensive agent. Additionally, the invention relates to a food and beverage product composition comprising a Boysenberry seed extract.

2. Background Art

It is widely known that triggers, such as western-style eating habits, lack of exercise, stress, smoking and hereditary factors, cause so-called typical lifestyle-related diseases, that is, hypertension and hyperlipidemia (for example, hypercholesteremia and hypertriglyceridemia). Among them, hypertension has the highest prevalence rate and is a disease that needs urgent preventive strategies from a health economic aspect.

In general, to ameliorate hypertensive symptoms, there have been conducted pharmacotherapies with diuretics, angiotensin-converting enzyme (ACE) inhibitors, angiotensin receptor antagonists, sympatholytic drugs, vasodilators or the like. These pharmacotherapies, however, have been reported to cause various side effects such as stomach malaise, diarrhea, and angioedema. Accordingly, there has been a social demand for the prevention and amelioration of hypertension using foods that are ordinarily edible with few side effects.

Boysenberry (*Rubus ursinus×idaeus* or *Rubus loganobaccus* and *Rubus baileyanus* Britt.) is said to be a crossbreed between blackberry and raspberry or a selected species of mutant wild berry species and is popular in Europe and America.

Regarding the functionality of Boysenberry-derived components, for example, an article (Kiyoko Kubomura, "Boysenberry as a Functional Food Ingredient", Journal of the Japan Association for the Integrated Study of Dietary Habits, vol. 16, No. 1, pp. 44-49, 2005) describes that Boysenberry contains a large amount of polyphenolic components with excellent antioxidant effect, such as anthocyanins and ellagic acid. The article predicts that anthocyanins included in fruits and leaves of Boysenberry are expected to have aging-preventing effect, cardiovascular function-protecting effect, diabetic exacerbation-inhibiting effect, hepatic damage-preventing effect, and the like. In addition, Japanese Patent Laid-Open Publication No. 2008-156306 has disclosed that a Boysenberry fruit-derived component can exhibit cancer-inhibiting effect. Furthermore, Japanese Patent Laid-Open Publication No. 2010-254590 has disclosed that Boysenberry-derived components, particularly a Boysenberry juice-derived component can exhibit pancreatic lipase-inhibiting effect.

In addition, WO 2010/092941 has disclosed that by combining a condensed tannin oligomer component, such as at least one of proanthocyanidins from dimer to tridecamer that are Boysenberry fruit-derived components and at least one organic acid, a vasodilator effect and an antihypertensive effect can be exhibited. Furthermore, an article (Ryo Furuuchi et al., "Analysis of proanthocyanidins in Boysenberry juice and the vasorelaxant effect in vitro", Proceedings of the 64th Annual Meeting of Japan Society of Nutrition and Food Science, 2010) has disclosed that a proanthocyanidin fraction from a Boysenberry fruit extract has a vasorelaxant effect and a combination thereof with citric acid as an organic acid can exhibit a strong vasorelaxant effect.

However, those articles have not described that Boysenberry extract alone has high antihypertensive activity. Additionally, there has been conducted no investigation focusing on Boysenberry seed.

Proanthocyanidins are a group of polyphenols contained in plants and fruits and also called "condensed tannins" or "non-hydrolyzable tannins". Proanthocyanidins are structurally a group of condensed polymerized substances consisting of flavan-3-ols as constituent units and are known to be present as various structural components depending on the structure of the constituent unit, the position of bonding, and the degree of polymerization. Depending on the differences in constituent unit, proanthocyanidins are classified into three subclasses, namely, procyanidins (condensed polymerized substances such as catechin, epicatechin, and epicatechin gallate), prodelphinidins (condensed polymerized substances such as gallocatechin, epigallocatechin, and epigallocatechin gallate), and propelargonidins (condensed polymerized substances such as afzelechin and epiafzelechin). Depending on the differences in bonding position, proanthocyanidins are largely divided into B type (a carbon-carbon bond between the constituent units is only $4\beta \rightarrow 8$ or $4\beta \rightarrow 6$) and A type (a carbon-carbon bond between the constituent units has at least one of $4\beta \rightarrow 8$ and $2\beta \rightarrow O \rightarrow 7$ or $4\beta \rightarrow 6$ and $2\beta \rightarrow O \rightarrow 7$).

It is known that components contained in plants and the structures and contents of the components largely vary depending on the kinds and tissue sites of the plants. In fact, regarding proanthocyanidins also, there is a report that proanthocyanidins contained in plants have significantly different unique structures, depending on the kinds of the plants from which they are derived. Such differences influence on health function and oral absorbability (M. Monagas, C. Gomez-Cordoves, B. Bartolome, O. Laureano, J. M. Ricardo da Silva, Monomeric, oligomeric, and polymeric flavan-3-ol composition of wines and grapes from *Vitis vinifera* L. Cv. Graciano, Tempranillo, and Cabernet Sauvignon. J. Agric. Food Chem. 2003, 51, p. 6475-6481).

When considering the bioavailability of proanthocyanidin, oral absorbability is concerned with whether proanthocyanidin can effectively exhibit its function or not, which thus has an extremely important meaning. Studies on oral absorbability of various kinds of proanthocyanidins have reported that oligomers with a low degree of polymerization are efficiently orally absorbed (see R. R. Holt, S. A. Lazarus, M. C. Sullards, Q. Y. Zhu, D. D. Schramm, J. F. Hammerstone, C. G. Fraga, H. H. Schmitz and C. L. Keen, Procyanidin dimer B2 [epicatechin-(4$\beta$-8)-epicatechin] in human plasma after the consumption of a flavanol-rich cocoa. Am. J. Clin. Nutr. 2002, 76, p. 798-804. T. Shoji, S. Masumoto, N. Moriichi, H. Akiyama, T. Kanda, Y. Ohtake, Y. Goda. Apple procyanidin oligomers absorption in rats after oral administration: Analysis of procyanidins in plasma using the porter method and High-Performance Liquid Chromatography/Tandem Mass Spectrometry. J. Agric. Food Chem. 2006, 54, p. 884-892).

Japanese Patent Laid-Open Publication No. 2003-212783 has disclosed antihyperglycemic and antihypertensive effects by proanthocyanidin contained in an extract obtained from a grape seed squeezed juice. It has described that a preferable proanthocyanidin has a molecular weight of 3000 or more (a degree of polymerization: 6.7 or more). However, its component and structure were different from those in proanthocyanidin found in Boysenberry seed and the effect of its activity was low.

Accordingly, there has been no report on the component, structure, and oral absorbability of Boysenberry seed-derived proanthocyanidin.

SUMMARY OF THE INVENTION

The present inventors have recently discovered that oral administration of a Boysenberry seed extract alone exhibits an excellent vasorelaxant effect (vasodilator effect) as compared to a Boysenberry fruit extract. In addition, by using a Boysenberry seed extract in hypertensive rats to study its influence on blood pressure, it has been found that the Boysenberry seed extract significantly suppresses blood pressure elevation. Furthermore, active components of the extract have been found to be proanthocyanidins. Then, results of analysis on components of a Boysenberry seed extract and a Boysenberry juice extract have showed that Boysenberry seed contains a large amount of proanthocyanidin dimers or trimers as compared to other sites of Boysenberry; the proanthocyanidins are dimeric or trimeric procyanidins and propelargonidins having a structure typical of Boysenberry seed; and additionally, the proanthocyanidins contained in Boysenberry seed are only proanthocyanidin dimers or trimers. Furthermore, the Boysenberry seed-derived proanthocyanidin dimers or trimers have actually exhibited high oral absorbability. In addition, the present inventors have also discovered a method for producing a high-quality antihypertensive agent and a proanthocyanidin dimer or trimer at low cost and efficiently from Boysenberry pomace including Boysenberry seed. The present invention is based on these findings.

Therefore, it is an object of the present invention to provide an effective and highly safe antihypertensive agent having antihypertensive effect that can contribute to the prevention and amelioration of hypertension and having very little risk of side effects even in continuous intake, and a method for producing the agents at low cost and efficiently. It is another object of the invention to provide a food and beverage product composition and a pharmaceutical product composition that include the antihypertensive agent. In addition, it is another object of the invention to provide a food and a beverage comprising a Boysenberry seed extract.

An antihypertensive agent according to the present invention includes a Boysenberry seed extract as an active ingredient.

According to a preferable aspect of the present invention, in the agent, the extract is a water extract, an organic solvent extract, or a water-containing organic solvent extract.

According to a more preferable aspect of the present invention, in the agent, the extract is a water-containing water-soluble organic solvent extract. In this case, still more preferably, the extract is a water-containing alcohol-based extract.

According to a still more preferable aspect of the present invention, in the agent, the extract is an extract of seed subjected to hydrothermal treatment.

According to a preferable aspect of the present invention, the agent includes a proanthocyanidin dimer or trimer extracted from Boysenberry seed, as the active ingredient.

According to a more preferable aspect of the present invention, the proanthocyanidin in the agent is procyanidin and/or propelargonidin.

According to a preferable aspect of the present invention, the Boysenberry seed in the agent is obtained from Boysenberry pomace.

According to another aspect of the present invention, there is provided a composition comprising the antihypertensive agent according to the invention.

According to further another aspect of the present invention, there is provided a food and beverage product composition comprising the antihypertensive agent according to the invention.

According to yet another aspect of the present invention, there is provided a food and beverage product composition comprising a Boysenberry seed extract.

According to a preferable embodiment of the present invention, the food and beverage product composition contains 4 wt % or more of a proanthocyanidin dimer or trimer.

According to a more preferable embodiment of the present invention, the food and beverage product in the food and beverage product composition is a health food, a functional food, a dietary supplement, or a food for specified health uses.

According to another aspect of the present invention, there is provided a method for producing a food and beverage product, the method comprising adding the antihypertensive agent according to the present invention in a material component of the food and beverage product.

According to another aspect of the present invention, there is provided a pharmaceutical product composition comprising the antihypertensive agent according to the present invention.

According to a preferable embodiment of the present invention, the pharmaceutical product composition is used for the treatment, prevention, or amelioration of a disease or condition capable of being treated, prevented, or ameliorated by antihypertensive effect. Herein, more preferably, the disease or condition is hypertension.

A method for producing an antihypertensive agent according to the present invention is a method for producing an antihypertensive agent comprising a Boysenberry seed extract as an active ingredient from Boysenberry pomace including Boysenberry seed and skin, the method comprising the steps of:

a) drying the pomace and selectively crushing a lump of the skin from the obtained dried pomace to sieve the seed;

b) grinding the seed obtained at the step a) into fine pieces, optionally extracting with a defatting organic solvent, removing an organic solvent portion, and drying a remaining portion, to obtain Boysenberry seed powder; and c) extracting an extract from the seed powder obtained at the step b) with water, an organic solvent, or a water-containing organic solvent, contacting an obtained extraction solution with a polyphenol adsorbent, eluting a component adsorbed to the adsorbent with an alcohol-based elution solvent, and optionally concentrating an obtained elution fraction, to obtain a target Boysenberry seed extract.

According to a preferable embodiment of the present invention, the selective crushing at the step a) of the method is to compress and crush the lump of the skin from the dried pomace by a crusher, while suppressing damage to the seed.

According to a preferable embodiment of the present invention, the method further comprises a step for hydrothermally treating the seed obtained at the step a) before grinding the seed into fine pieces at the step b).

According to a preferable embodiment of the present invention, the method further comprises a step of:

d) partitioning the Boysenberry seed extract obtained at the step c) with a solvent having an octanol/water partition coefficient of 0 to 1 and water, and optionally concentrating an obtained solvent phase, to obtain a partitioned concentrate of Boysenberry seed extract. Herein, more preferably, the solvent with the octanol/water partition coefficient of 0 to 1 is one or more solvents selected from a group consisting of ethyl acetate, methyl acetate, ethyl formate, and butanol.

According to another aspect of the present invention, there is provided a method for suppressing blood pressure elevation, comprising administering or feeding to a mammal an effective dose of the Boysenberry seed extract or the proanthocyanidin dimer or trimer extracted from Boysenberry seed, as the active ingredient.

According to another aspect of the present invention, there is provided a method for treating, preventing, or ameliorating a disease or a condition capable of being treated, prevented, or ameliorated by suppressing blood pressure elevation, the method comprising administering or feeding to a mammal a therapeutically effective dose of the Boysenberry seed extract or the proanthocyanidin dimer or trimer extracted from Boysenberry seed, as the active ingredient.

According to a preferable embodiment of the present invention, the disease or condition in the method is hypertension, a lifestyle-related disease, or a condition associated with them.

According to another aspect of the present invention, there is provided a use of the Boysenberry seed extract or the proanthocyanidin dimer or trimer extracted from Boysenberry seed, as the active ingredient, for manufacturing an antihypertensive agent.

According to another aspect of the present invention, there is provided a use of the Boysenberry seed extract or the proanthocyanidin dimer or trimer extracted from Boysenberry seed, as the active ingredient, for manufacturing a composition used for the treatment, prevention, or amelioration of a disease or a condition capable of being treated, prevented, or ameliorated by suppressing blood pressure elevation.

According to a preferable embodiment of the present invention, the disease or condition in the use is hypertension, a lifestyle-related disease, or a condition associated with them.

A method for producing a proanthocyanidin dimer or trimer according to the present invention is a method for producing a proanthocyanidin dimer or trimer from Boysenberry pomace including Boysenberry seed and skin, the method comprising the steps of:

a) drying the pomace and selectively crushing a lump of the skin from the obtained dried pomace to sieve the seed;

b) grinding the seed obtained at the step a) into fine pieces, optionally extracting with a defatting organic solvent, removing an organic solvent portion, and drying a remaining portion, to obtain Boysenberry seed powder; and c) extracting an extract from the seed powder obtained at the step b) with water, an organic solvent, or a water-containing organic solvent, contacting an obtained extraction solution with a polyphenol adsorbent, eluting a component adsorbed to the adsorbent with an alcohol-based elution solvent, and optionally concentrating an obtained elution fraction, to obtain a target proanthocyanidin dimer or trimer.

According to an antihypertensive agent of the present invention, elevation of blood pressure can be suppressed effectively and safely. Therefore, the antihypertensive agent of the invention is significantly effective in the prevention and amelioration of hypertension. In addition, the antihypertensive agent of the invention uses a Boysenberry extract used also as a food, so that the agent has very little risk of side effects even in continuous intake and thus is highly safe. Moreover, according to a production method of the invention, Boysenberry pomace as an unused resource is used as raw material. Thus, a high-quality antihypertensive agent can be produced efficiently and at low cost. In addition, since proanthocyanidins contained in Boysenberry seed are only dimeric or trimeric proanthocyanidins, the method of the invention can also produce a proanthocyanidin dimer or trimer. Additionally, according to the invention, there can be provided a food and beverage product composition and a pharmaceutical product composition including the antihypertensive agent, or a food and beverage product composition including a Boysenberry seed extract. Accordingly, by taking them, suppression of blood pressure elevation in the body can be effectively achieved. Furthermore, the antihypertensive agent according to the invention, and the food or beverage product composition and the pharmaceutical product composition including them are effective in the treatment, prevention, and amelioration of hypertension, and also in the prevention and amelioration of lifestyle-related diseases including circulatory diseases such as high blood pressure-induced arteriosclerosis, heart disease, cerebral apoplexy, and kidney disease.

DETAILED DESCRIPTION OF THE INVENTION

Antihypertensive Agents/Production Method

Figure 1:
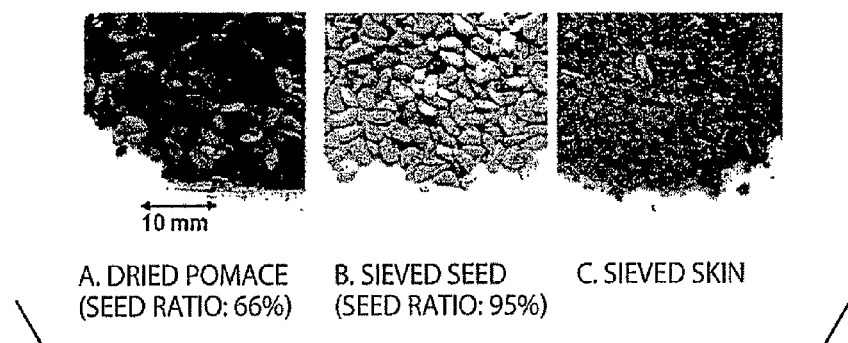
FIG. 1 shows photographs showing a state of seed and skin in dried Boysenberry pomace and states of the seed and the skin after sieving (sieving separation) at a step a) of Example 1 of the present invention.

An antihypertensive agent according to the present invention includes, as described above, a Boysenberry seed extract as an active ingredient. The antihypertensive agent according to the invention, preferably, includes a proanthocyanidin dimer or trimer extracted from Boysenberry seed, as the active ingredient.

Boysenberry Seed

Boysenberry (*Rubus ursinus*×*idaeus* or *Rubus loganobaccus* and *Rubus baileyanus* Britt.) is thought to be a breed produced by cross-breeding among blackberry, raspberry, and loganberry. Its fruit is characterized by vivid purple color, rich fragrance and good taste with moderate sweetness and acidity. Boysenberry is rich in calcium, iron, zinc, vitamin A, folic acid, niacin, and vitamin C, and contains the nutrients in good balance.

In the present invention, "Boysenberry seed" means a portion of a Boysenberry fruit in which the juice, pulp, and skin have been removed from the fruit.

Active Ingredient

In the present invention, the term "active ingredient" means a component required to exhibit antihypertensive effect intended by the invention.

The active ingredient in the present invention is an extract of Boysenberry seed and its main component. Thus, it is preferably a proanthocyanidin dimer or trimer extracted from Boysenberry seed.

In the present invention, the term "proanthocyanidin dimer or trimer" refers to a group of polyphenols, which is a group of substances whose constituent units are composed of flavan-3-ols and in which two or three constituent units of flavan-3-ols are bound by condensation polymerization. Proanthocyanidins are classified into three subclasses, namely, procyanidins (condensation polymers such as catechin, epicatechin, and epicatechin gallate), prodelphinidins (condensation polymers such as gallocatechin, epigallocatechin, and epigallocatechin gallate), and propelargonidins (condensation polymers such as afzelechin and epiafzelechin).

According to a preferable aspect of the present invention, the proanthocyanidin is procyanidin and/or propelargonidin. Procyanidin is a substance formed from constituent units of catechin and epicatechin, and propelargonidin is a substance formed from constituent units of afzelechin and epiafzelechin.

In oral administration of the antihypertensive agent according to the present invention including a proanthocyanidin dimer or trimer as an active ingredient, all those components are absorbed and transferred into the blood (see Examples 4 and 7 described below). Thereby, the agent acts efficiently in vivo and can exhibit an effective antihypertensive effect.

Extracts

In the present invention, the "extract" is obtainable by extraction from Boysenberry seed and means an extraction solution, a diluent thereof, a concentrated liquid thereof, an essence thereof, or their dried products or dried powders. Herein, extraction operation includes compression extraction and solvent extraction with water and an organic solvent, and if needed, treatment such as adsorption, concentration, filtration, or centrifugal separation may be additionally performed.

Extraction of Active Ingredient

According to a preferable aspect of the present invention, the extract of the invention can be obtained by solvent extraction of Boysenberry seed using water or an organic solvent.

Herein, the organic solvent is not specifically restricted as long as it can extract an extract having a desired effect, and preferred is an organic solvent having water solubility (water miscibility). In the case of a water-soluble organic solvent, it can be used as a mixture with water, and such a water-containing organic solvent is also usable. Therefore, for example, if the organic solvent is a water-soluble alcohol-based solvent, the above-described extract includes also a water-containing alcohol-based solvent extract, which is obtained by extraction with an alcohol-based solvent that contains water in a certain ratio.

Specific examples of water-soluble organic solvents include methanol, ethanol, isopropanol, acetonitrile, butanol, propylene glycol, butylene glycol, glycerin, acetone, ethyl acetate, ethyl formate, methyl acetate, and methyl ethyl ketone. These can be used for extraction, as a mixture of two or more kinds thereof or can be used as a mixture with water if possible.

From the viewpoint of compatibility with a food and beverage product composition and a pharmaceutical product composition, for a safety aspect considering a remaining solvent, a preferable extraction solvent to be used is water alone or a mixture of water and ethanol.

Therefore, according to a preferable aspect of the present invention, the extract is a water extract, an organic solvent extract, or a water-containing organic solvent extract. The extract is more preferably a water-containing organic solvent extract, still more preferably a water-containing alcohol-based solvent extract or a water-containing acetone extract, additionally further more preferably a water-containing ethanol extract, and particularly preferably a 50 to 80% water-containing ethanol extract.

According to a preferable aspect of the present invention, the extract of the invention is a Boysenberry seed extract. Specifically, an extraction solution of Boysenberry seed using water, an organic solvent, or a water-containing organic solvent is contacted with a polyphenol adsorbent, and then, a component adsorbed to the adsorbent is eluted with a solvent, whereby a Boysenberry seed extract can be obtained as an elution fraction. Herein, this extract is preferably a concentrate of the obtained elution fraction.

Herein, the polyphenol adsorbent can be any as long as it can adsorb and elute a polyphenol component contained in the extraction solution. For example, there may be mentioned synthetic adsorbents, activated carbon, ion exchange resins, polyvinyl pyrrolidone, diatomaceous earth, or combinations thereof.

The polyphenol adsorption and elution operation are preferably performed in a form of column chromatography. In this case, the polyphenol adsorbent is used as a packing material. The material is preferably a polystyrene-based synthetic adsorbent composed of a styrene-divinylbenzene copolymer, and more preferably a commercially available Amberlite XAD-7HP (Organo Corp.) or Diaion HP20 (Mitsubishi Chemical Corp.). An adsorbed polyphenol component can be eluted, for example, with an alcohol-based solvent, preferably ethanol, after washing with water.

Concentration method varies with solvent and is not specifically restricted as long as the method does not denature the active components contained in a solution and can increase a concentration of the active components. As examples of the concentration method, there may be mentioned concentration at reduced pressure by an evaporator, drying, freeze-drying, gel filtration concentration, film concentration, or combinations thereof. Regarding the concentration method, for example, if the solvent is an alcohol-based solvent such as ethanol, preferably, ethanol contained in a solution is concentrated at reduced pressure by an evaporator and, additionally, the solution is freeze-dried. This concentration step may be performed in an extraction solution before contacting the solution with a polyphenol adsorbent.

Pulverization of Seed

According to a preferable aspect of the present invention, as Boysenberry seed used for extraction, Boysenberry seed powder is used. Specifically, Boysenberry seed powder can be obtained by grinding the seed into fine pieces before extracting an extract as the active ingredient from Boysenberry seed. The seed powder is preferably defatted seed powder obtained by extracting lipids content from the seed powder, removing an organic solvent portion, and drying a remaining portion.

Herein, the method for grinding the seed into fine pieces is not specifically restricted as long as it can grind the seed into pieces with a desired size. Herein, the particle diameter of a grinded product of the seed grinded into fine pieces varies with extraction conditions. For example, the powder has a particle diameter of 0.1 to 5 mm, and of preferably 0.2 to 2 mm. It is more advantageous as the particle diameter becomes smaller, because extraction efficiency increases. Meanwhile, it is also necessary to consider a particle diameter capable of facilitating a solid-liquid separation step. As a method for obtaining such powder, for example, there may be mentioned pulverization of seed by a grinder, such as a colloid mill or a ball mill. Pulverization of the seed can increase the extraction efficiency of the active ingredient.

The defatting organic solvent is not specifically restricted as long as it can extract lipid content without almost the extraction of the active ingredient in the defatting organic solvent. A preferable defatting organic solvent is hexane. Extraction time can be suitably adjusted. Using the defatted seed powder can prevent lipid content from being mixed during the extraction of the active ingredient.

Hydrothermal Treatment of Seed

According to a more preferable aspect of the present invention, the extract is an extract of seed subjected to hydrothermal treatment. Specifically, the extract of hydrothermally treated seed can be obtained by hydrothermally treating seed before grinding the seed into fine pieces.

The present inventors unexpectedly discovered that, by the hydrothermal treatment of the seed before grinding them into fine pieces, without almost the elution of proanthocyanidins into water, polyphenol contaminants such as ellagitannins, which are non-proanthocyanidins, can be eluted into water. The present inventors also discovered that water treatment or hydrothermal treatment of the seed grinded into fine pieces causes the elution of a large amount of proanthocyanidins, together with ellagitannins, into water. Such a property is completely different from a conventionally known property of grape seed, as shown in Example 1 of Japanese Translation of PCT Application No. 2009-512638.

Herein, the hydrothermal treatment means a treatment with hot water of preferably 50° C. or higher, more preferably 70° C. or higher, and still more preferably 80° C. or higher. Time for the hydrothermal treatment is preferably 30 to 120 minutes, and more preferably 50 to 70 minutes. With the hydrothermal treatment, ellagitannins as the polyphenol contaminants contained in the seed are eluted into hot water and removed from the seed, whereby a good-quality extract with a high content of proanthocyanidins can be produced. Additionally, sterilization of the seed can also be performed.

Selection of Seed from Pomace

According to another preferable aspect of the present invention, as Boysenberry seed used for extraction, seed obtained from Boysenberry pomace is used. Specifically, Boysenberry pomace can be obtained by drying Boysenberry pomace including the Boysenberry seed and skin, selectively crushing a lump of the skin from the obtained dried pomace, and then sieving the seed.

Boysenberry pomace is pomace (by-product) discharged in a large amount upon the juice extraction and concentration of Boysenberry fruit and generally contains 40 to 50 wt % of water.

Herein, drying method can be any as long as it does not denature proanthocyanidins in the Boysenberry pomace and can dry the residue into a desired drying state. For example, there may be mentioned hot-air drying, vacuum drying, freeze-drying, or steam drying, and preferred is hot-air drying. Hot-air drying can be performed in an air flow of preferably 50 to 100° C., and more preferably 60 to 80° C. The desired drying state refers to a state in which loss on drying was less than 5%. The drying can reduce a viable bacterial count in dried pomace by thousands or more.

The lump of the skin means a lump consisting of skin, pulp, and the other juice leavings, except for the seed, which are included in the dried pomace.

Herein, selective crushing means to crush only the lump of the skin except for the seed from the dried pomace, where the seed is damaged but the damage is minimized. As a selectively crushing method, for example, there may be mentioned compression crushing by a crusher, separation and removal of a lump of the skin by a visual method, or the like.

According to a more preferable aspect of the present invention, the selective crushing refers to compression crushing of the lump of the skin attached to the seed from the dried pomace, while suppressing damage to the seed. Herein, as a compression crushing method, for example, there may be mentioned a roll crusher, a ball crusher, a rod crusher, a manual type crusher, or the like, which can be used alone or in combination for crushing. The crusher to be used is, in terms of a fact that it can selectively crush only the lump of skin while minimizing crushing of the seed, preferably, a rubber roll-shaped or brush-shaped ball crusher, and more preferably a ball crusher using a nylon-coated ball.

Sieving of seed (sieving separation) means to separate, using a sieve, the crushed product obtained by the selective crushing of the above dried pomace into powder of a crushed lump of the skin as a portion passing through the sieve and non-crushed seed that cannot pass through the sieve to obtain high purity seed. The sieve has a mesh opening of, for example, 0.5 to 2.0 mm, and preferably of 1.0 mm.

Figure 2:
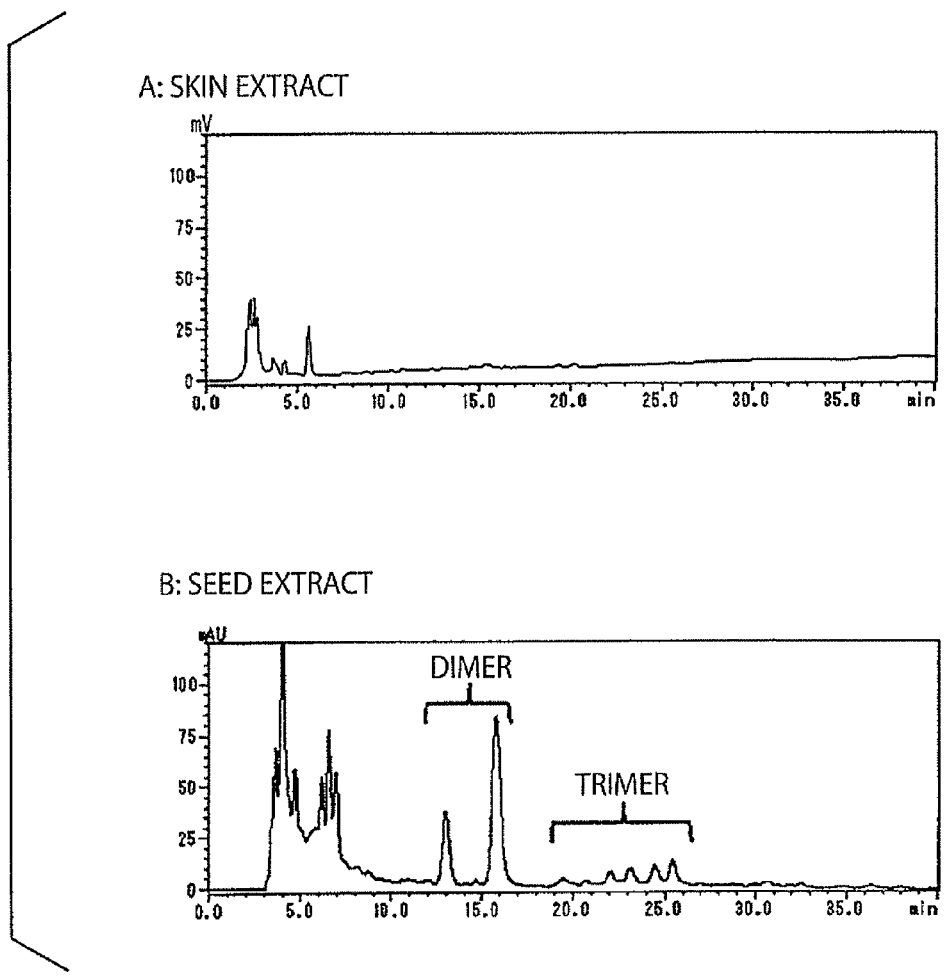
FIG. 2 shows data showing results of HPLC analysis on a seed extract (A) or a skin extract (B) obtained in Example 1.

Herein, a ratio of the seed after sieving is preferably 95% or more. As shown in FIG. 2 of Example 1 described below, the present inventors discovered that the skin does not contain proanthocyanidins and contains polyphenol contaminants such as ellagitannins, which are non-proanthocyanidin components. Accordingly, increasing the ratio of the seed can prevent mixing of polyphenol contaminants caused due to the presence of the skin. In addition, thereby, there can be produced a high-quality extract with a high content of proanthocyanidins. Furthermore, the use of Boysenberry pomace that is an unused resource can reduce production cost.

The skin obtained after sieving separation is rich in ellagitannins and thus can be used for stock feed, as raw material of an ellagitannin component.

Partition and Concentration of Extract

Furthermore, according to a preferable aspect of the present invention, the extract is a partitioned concentrate of Boysenberry seed extract. Specifically, an obtained Boysenberry seed extract is partitioned with a solvent having an octanol/water partition coefficient (Log Pow) of 0 to 1 and water, whereby the partitioned concentrate of Boysenberry seed extract can be obtained as a solvent phase. Herein, this concentrate is preferably a concentrate of the obtained solvent phase. As the concentration method, the above-mentioned concentration method can be used.

The solvent having the octanol/water partition coefficient of 0 to 1 is preferably one or more solvents selected from a group consisting of ethyl acetate, methyl acetate, ethyl formate, and butanol, and more preferably ethyl acetate.

The octanol/water partition coefficient of Boysenberry proanthocyanidins was in a range of −1.0 to 0.1 and the coefficient of ellagitannins as polyphenol contaminants was −2.0 or less (see Example 1 described below). The above-described partition has an advantage in that the partition can separate Boysenberry proanthocyanidins into a solvent phase and ellagitannins into a water phase. The partition can further increase the content of proanthocyanidins as the active components in a solution.

The extract is usually easily water-soluble and can maintain a stable property as a solution. Thus, the extract is excellent in miscibility with components that can be ordinarily added into food and beverage product composition and a pharmaceutical product composition. In addition, since the extract is a component contained in the food, it is nonpoisonous and excellent in safety. Accordingly, the antihypertensive agent including them as the active ingredient exhibits excellent safety, has very little risk of side effects, and can be easily taken by appropriately incorporating in daily meals.

The antihypertensive agent according to the present invention can be used alone, or can be included as an additive in various compositions of food and beverage products, pharmaceutical products, and the like to obtain compositions having antihypertensive effect. The obtained compositions can be effectively used not only for the treatment, prevention, and amelioration of hypertension but also for the prevention and amelioration of lifestyle-related diseases including circulatory diseases such as high blood pressure-induced arteriosclerosis, heart disease, cerebral apoplexy, and kidney disease. Thus, according to a preferable aspect of the invention, there is provided a composition comprising the antihypertensive agent.

Method for Producing Antihypertensive Agents

In a preferable embodiment of the present invention, a method for producing an antihypertensive agent according to the present invention is a method comprising the steps of:

a) drying Boysenberry pomace including Boysenberry seed and skin and selectively crushing a lump of the skin from the obtained dried pomace to sieve the seed;

b) grinding the seed obtained at the step a) into fine pieces, optionally extracting with a defatting organic solvent, removing an organic solvent portion, and drying a remaining portion, to obtain Boysenberry seed powder; and c) extracting an extract from the seed powder obtained at the step b) with water, an organic solvent, or a water-containing organic solvent, contacting an obtained extraction solution with a polyphenol adsorbent, eluting a component adsorbed to the adsorbent with an alcohol-based elution solvent, and optionally concentrating an obtained elution fraction, to obtain an extract usable as an active ingredient (a Boysenberry seed extract). This method can produce a safe antihypertensive agent from, as raw material, Boysenberry pomace that is an unused resource, at low production cost and efficiently.

In a more preferable embodiment of the present invention, the method for producing an antihypertensive agent according to the present invention is a method further comprising a step of:

d) partitioning the Boysenberry seed extract obtained at the step c) with a solvent having an octanol/water partition coefficient of 0 to 1 and water, and optionally concentrating an obtained solvent phase, to obtain a partitioned concentrate of extract usable as an active ingredient (a partitioned concentrate of Boysenberry seed extract). This method can further increase the content of proanthocyanidins in the seed, which thus allows for the production of a high-quality antihypertensive agent having a high specific activity and good usability.

In an additionally preferable embodiment of the present invention, the method for producing an antihypertensive agent according to the present invention is a method further comprising a step for hydrothermally treating the seed obtained at the step a) before grinding the seed into fine pieces at the step b). This method can remove polyphenol contaminants contained in the seed before the extraction of proanthocyanidin as the active ingredient, so that the method can efficiently produce a high-quality antihypertensive agent having a higher content of proanthocyanidins.

The method for producing an antihypertensive agent according to the present invention can be used also as a method for producing a high-quality proanthocyanidin dimer or trimer at low production cost and efficiently.

Specifically, in a preferable embodiment of the present invention, a method for producing a proanthocyanidin dimer or trimer according to the present invention comprises the steps of:

a) drying Boysenberry pomace including Boysenberry seed and skin and selectively crushing a lump of the skin from the obtained dried pomace to sieve the seed;

b) grinding the seed obtained at the step a) into fine pieces, optionally extracting with a defatting organic solvent, removing an organic solvent portion, and drying a remaining portion, to obtain Boysenberry seed powder; and c) extracting an extract from the seed powder obtained at the step b) with water, an organic solvent, or a water-containing organic solvent, contacting an obtained extraction solution with a polyphenol adsorbent, eluting a component adsorbed to the adsorbent with an alcohol-based elution solvent, and optionally concentrating an obtained elution fraction.

In a more preferable embodiment of the present invention, the method for producing a proanthocyanidin dimer or trimer according to the present invention is a method further comprising a step of:

d) partitioning the Boysenberry seed extract obtained at the step c) with a solvent having an octanol/water partition coefficient of 0 to 1 and water, and optionally concentrating an obtained solvent phase.

In an additionally preferable embodiment of the present invention, the method for producing a proanthocyanidin dimer or trimer according to the present invention is a method further comprising a step for hydrothermally treating the seed obtained at the step a) before grinding the seed into fine pieces at the step b).

Uses

The Boysenberry seed extract or the proanthocyanidin dimer or trimer, as the active ingredient according to the present invention, has antihypertensive effect (see Examples 2 and 3 described below) and also has a vasodilator effect and a vasorelaxant effect (see Example 5 described below).

Herein, the "antihypertensive effect" includes having the effect of suppressing blood pressure elevation, as well as blood pressure-lowering effect, vasodilator effect, vasorelaxant effect, blood circulation-improving effect, and reduction and alleviation effect of symptoms such as headache associated with vascular circulation function.

Additionally, herein, "the effect of suppressing blood pressure elevation" means the activity of suppressing blood pressure elevation in the body, which allows for the treatment, prevention, or amelioration of hypertension and the treatment, prevention, or amelioration of lifestyle-related diseases.

Therefore, the active ingredient according to the present invention can be used for the treatment, prevention, or amelioration of a disease or a condition capable of being treated, prevented, or ameliorated by antihypertensive effect. Herein, the disease or the condition capable of being treated, prevented, or ameliorated by antihypertensive effect is hypertension, a lifestyle-related disease, or a condition associated with them.

In the present description, the expression "the treatment, prevention, or amelioration" of a disease or a condition is used as a meaning including the control, retardation of progress, alleviation, development prevention, reoccurrence prevention, and inhibition of a disease or a condition.

According to another aspect of the present invention, there is provided a method for suppressing blood pressure elevation comprising administering or feeding to a mammal an effective dose of the extract or the proanthocyanidin dimer or trimer, which is the active ingredient of the present invention. Herein, the "effective dose" refers to a sufficient amount capable of exhibiting a blood pressure elevation suppressing activity within a desired region in the body by administration.

According to another aspect of the present invention, there is provided a method for treating, preventing, or ameliorating a disease or a condition capable of being treated, prevented, or ameliorated by suppressing blood pressure elevation, the method including administering or feeding to a mammal a therapeutically effective dose of the extract or the proanthocyanidin dimer or trimer, which is the active ingredient of the present invention. Herein, the "theoretically effective dose" refers to an amount sufficient to relieve one or more symptoms usually accompanying a disease or a condition whose treatment is desired. In the case of a preventive use, the term refers to an amount sufficient to prevent or retard the development of a disease or a condition. Herein, the disease or the condition is preferably hypertension, a lifestyle-related disease, or a condition associated with them.

According to another aspect of the present invention, there is provided a use of the extract or the proanthocyanidin dimer or trimer, which is the active ingredient of the present invention, for manufacturing an antihypertensive agent.

According to another aspect of the present invention, there is provided a use of the extract or the proanthocyanidin dimer or trimer, which is the active ingredient of the present invention, for manufacturing a composition used for the treatment, prevention, or amelioration of a disease or a condition capable of being treated, prevented, or ameliorated by suppressing blood pressure elevation. Herein, the disease or the condition is preferably hypertension, a lifestyle-related disease, or a condition associated with them.

Composition: a Food and Beverage Product Composition and a Pharmaceutical Product Composition As described above, according to the present invention, there is provided a composition comprising the antihypertensive agent according to the present invention. Thus, these compositions comprise a Boysenberry seed extract or a proanthocyanidin dimer or trimer extracted from Boysenberry seed, as the active ingredient.

Herein, to "comprise as the active ingredient" means to include a case in which, while it is obvious that the composition according to the present invention includes an active ingredient having an amount (namely, an effective dose) sufficient to exhibit a desired antihypertensive effect and can include a physiologically acceptable carrier according to a desired product form, the composition may also include any other auxiliary component that can be used in combination.

According to a preferable aspect of the present invention, the composition comprising the antihypertensive agent according to the present invention is a food and beverage product composition. Such a food and beverage product composition can be produced, for example, by a production method comprising adding the antihypertensive agent according to the present invention in a material component of a food and beverage product.

According to a preferably aspect of the present invention, the composition comprising the antihypertensive agent according to the present invention is a pharmaceutical product composition. Such a pharmaceutical product composition is used for the suppression of blood pressure elevation in the body.

According to another aspect of the present invention, the composition of the present invention comprising a Boysenberry seed extract. Herein, the expression "composition comprising a Boysenberry seed extract" means a composition that does not include any extract derived from Boysenberry's skin, pulp, and any other tissue, except for its seed.

In the present invention, the food and beverage product means any product other than a pharmaceutical product composition and may be a solution, a suspension, an emulsion, powder, a solid molded product, or the like. The food and beverage product is not specifically restricted as long as it is in a form that can be taken orally. Specifically, for example, there may be mentioned ready-to-eat foods such as instant noodles, boil-in-the bag foods, canned foods, foods cooked by microwave, instant soups and miso soups, and freeze-dried foods; beverages such as soft drinks, fruit juice drinks, vegetable drinks, soybean milk drinks, coffee drinks, tea drinks, powder drinks, concentrated drinks, and alcohol drinks; flour products such as breads, pasta, noodles, pancake mixes, and crumbs; sweets such as candies, caramels, chewing gums, chocolates, cookies, biscuits, cakes, pies, snacks, crackers, Japanese sweets, and dessert sweets; condiments such as sauces, processed tomato condiments, flavoring condiments, cooking mixes, dipping sauces, dressings, broths, and seasonings such as curry and stew mixes; oils and fats such as processed oils and fats, butter, margarine, and mayonnaise; milk products such as milk drinks, yogurts, lactic fermenting beverages, ice creams, and creams; processed agricultural products such as canned agricultural products, jams and marmalades, and cereals; and frozen foods.

Additionally, the food and beverage product includes also heath foods, functional foods, dietary supplements, foods for specified health uses, patient foods, infant formula milks, milk powders for pregnant and lactating women, or categories such as food and beverage products with an indication of disease risk reduction.

According to another aspect of the present invention, there can be provided a food and beverage product including an effective dose of the extract or the proanthocyanidin dimer or trimer extracted from Boysenberry seed, the product having an indication of a function of treating, preventing, or ameliorating a disease or a condition capable of being treated, prevented, or ameliorated by suppressing blood pressure elevation. According to still another aspect of the present invention, there can be provided a food and beverage product including an effective dose of the extract, the product having an indication of an antihypertensive ability.

Thus, the food and beverage product according to the present invention can be provided, for example, as a food and beverage product suited for consumers expecting the amelioration or alleviation of hypertensive conditions, namely, as a so-called food for specified health uses. The food for specified health uses mentioned herein can refer to a food and beverage product that may be subjected to some legal limitations in individual countries from a health viewpoint upon the production, sale, or the like of the food and beverage product for purposes of a disease or a condition capable of being treated, prevented, or ameliorated by suppressing blood pressure elevation, the prevention, amelioration, or condition alleviation of hypertension, and the treatment, prevention, amelioration, or the like of lifestyle-related diseases. Such a food and beverage product can also be a food and beverage product with an indication showing that the product can reduce a disease risk, that is, a food and beverage product with an indication of reduced disease risk attached thereto.

In the present invention, the pharmaceutical product composition refers to a product prepared as an oral formulation or a non-oral formulation according to a common method by combining with an additive acceptable for pharmaceutical preparation. Oral formulation can be in a form of solid formulation, such as tablet, powdered medicine, subtle granule, granule, capsule, pill, or sustained release drug, and in a form of liquid formulation, such as solution, suspension, or emulsion. In addition, non-oral formulation can be in a form of injection or suppository. In terms of simplicity, preferred are oral formulations. As additives acceptable for pharmaceutical preparation, for example, there may be mentioned vehicles, stabilizers, preservatives, wetting agents, emulsifiers, lubricants, sweeteners, colorants, flavors, buffers, antioxidants, pH adjusters, and the like.

It is difficult to uniformly define a content of the antihypertensive agent or the Boysenberry seed extract in the composition such as a food and beverage product composition or a pharmaceutical product composition depending on the kind and form of composition, the purposes of prevention and amelioration, and the like. However, the content thereof can be any amount as long as the content of a proanthocyanidin dimer or trimer contained as the active ingredient of the antihypertensive agent or contained in the Boysenberry seed extract is preferably 1 wt % or more, and more preferably 4 wt % or more. The content thereof in the composition can be appropriately determined by considering a composition intake amount per day such that a necessary intake amount of the active ingredient per day can be taken.

The intake amount of the composition such as a food and beverage product composition or a pharmaceutical product composition is appropriately determined according to individual cases in consideration of the form (dosage form in the case of pharmaceutical product) and the age, weight, sex, purpose of intake, and the like of a person who intends to take the product or the composition. For example, the intake amount is, in terms of a Boysenberry seed extract (such as a seed extract produced in Example 1), 0.5 mg/kg or more, preferably 2 mg/kg or more, more preferably 3 mg/kg, further more preferably 5 mg/kg or more, and particularly preferably 10 mg/kg or more. This can be taken in or administered once daily or few times daily by dividing into a few doses per day.

EXAMPLES

The present invention will be described in detail with reference to the following Examples, although the invention is not limited thereto.

Example 1

Preparation of Boysenberry Seed Extracts Containing Proanthocyanidins from Boysenberry Pomace as Raw Material (a) Preparation of Seed from Pomace Two kg of Pomace discharged in the production of Boysenberry fruit juice was placed in a hot-air drying machine (STAC-P400K manufactured by Shimadzu Rika Corp.) and dried at 70° C. for 20 hours to obtain 1.1 kg of dried Boysenberry pomace (seed substance purity: 66%; see FIG. 1-A). The obtained dried pomace was placed in a rubber roll-type roll crusher (a medium-sized testing huller: ST-50A manufactured by Fujiwara Scientific Co., Ltd.) to be processed for 30 minutes. Next, the processed residue was placed in a ball crusher (a small-sized ball mill: AV-1 manufactured by AS ONE Corp.) using a nylon-coated ball (particle diameter: 6.4 mm, a nylon-coated iron ball manufactured by AS ONE Corp.) and processed for 30 minutes to selectively crush a lump of skin included in the dried pomace while suppressing damage to seed. The selectively crushed pomace was sieved through a sieve with a mesh opening of 1.0 mm (manufactured by TAKESHOW Co., Ltd.) to obtain 642 g of Boysenberry seed (seed substance purity: 95%, see FIG. 1-B, drying loss: 1.5 wt %) as a portion of the residue that could not pass through the sieve and left thereon and 376 g of Boysenberry skin powder as a portion thereof that passed through the sieve (see FIG. 1-C).

Additionally, except that processing time by the ball crusher with the nylon-coated ball was set to 1 hour, the same processing as above was performed to obtain 628 g of seed with a seed substance purity of 97%.

(b) Preparation of Defatted Seed Powder or Hydrothermally-Treated Defatted Seed Powder Using a grinder (Grindmix GM200 manufactured by Retsch Co. Ltd.), 100 g of the obtained Boysenberry seed was grinded into fine pieces (particle diameter: approximately 0.2 to 2 mm), and hexane (obtained from Kanto Chemical Co., Inc.), which is three times by weight as much as the obtained seed powder, was added to the powder and the mixture was stirred at room temperature for 1 hour to extract lipids contained in the seed powder. After that, the resultant product was allowed to stand, hexane was removed, and a remaining portion (deposit) was dried in the air to obtain 95 g of the defatted Boysenberry seed powder.

Additionally, the obtained Boysenberry seed was processed in a hot water of 90° C. for 1 hour and dried at 70° C. to obtain hydrothermally treated seed. The same processing as above was performed also on the hydrothermally treated seed to obtain hydrothermally-treated defatted Boysenberry seed powder.

(c) Preparation of Seed Extract or Hydrothermally-Treated Seed Extract

To 100 g of the defatted Boysenberry seed powder or 100 g of the hydrothermally-treated defatted Boysenberry seed powder was added 1.0 L of 60% ethanol (obtained from Wako Pure Chemical Industries, Ltd.), and the mixture was stirred at 70° C. for 3 hours to extract a polyphenol component contained in the seed powder. The obtained extraction solution was concentrated at reduced pressure by an evaporator, and then, made into powder with a freeze-drying machine (DC-400 manufactured by Yamato Scientific Co., Ltd.) to obtain 5.30 g of a seed powder extract (content of proanthocyanidins: 0.7%) or 3.98 g of a hydrothermally-treated seed powder extract (content of proanthocyanidins: 1.0%). Each of the extracts was dissolved in deionized water, then, the solution was loaded on a polyphenol-adsorbing resin column (Amberlite XAD-7HP manufactured by Organo Corp.), followed by washing with deionized water equivalent to a column volume. After that, the adsorption column was eluted with an amount of ethanol (99.5% or more) two times the column volume. The obtained elution solution was concentrated at reduced pressure and made into powder with the freeze-drying machine to obtain 1.80 g of a Boysenberry seed extract (content of proanthocyanidins: 4.2%) or 1.26 g of a hydrothermally-treated seed extract (content of proanthocyanidins: 6.5%).

Regarding the Boysenberry skin powder obtained in the above (a), except that, in the above (c), freeze drying was not performed after extraction of the polyphenol component with ethanol and concentration at reduced pressure, the same processing as in the above-described seed extract was performed. As a result, 0.8 g of a skin extract was obtained.

(d) Preparation of Partitioned Concentrate of Seed Extract or Partitioned Concentrate of Hydrothermally-Treated Seed Extract (Partition Step)

1) Setting of Octanol/Water Partition Coefficient

To perform partition of proanthocyanidins contained in Boysenberry seed, there were obtained octanol/water partition coefficients of proanthocyanidins and ellagitannins as polyphenol contaminants, which are contained in the Boysenberry seed. Specifically, to 10 mg of the Boysenberry seed extract were added 3 mL of octanol and 3 mL of water. The mixture was intensely stirred for 30 minutes and allowed to stand for 10 minutes to separate into an octanol phase and a water phase. Amounts of polyphenol components contained in both phases were determined using HPLC to obtain a partition coefficient. As a result, the partition coefficient of proanthocyanidins was in the range of −1.0 to 0.1, whereas the coefficient of ellagitannins as the polyphenol contaminant was −2.0 or less. Therefore, as an organic solvent used upon the partition of proanthocyanidins of Boysenberry seed, there was selected a slightly hydrophobic organic solvent having a permittivity of 0 to 1. The solvent within the range is slightly hydrophobic and thus can dissolve a hydrophilic (that is, the octanol/water partition coefficient is small) substance.

2) Partition Step

To 10 mL of deionized water, 1.0 g of the seed extract or 1.0 g of the hydrothermally-treated seed extract was each dissolved, and the each solution was partitioned 7 times with 100 mL of ethyl acetate. Each ethyl acetate phase was concentrated and dried to obtain 0.24 g of a partition concentrate of seed extract (content of proanthocyanidins: 8.9%) or 0.26 g of a partitioned concentrate of hydrothermally-treated seed extract (content of proanthocyanidins: 13.6%).

(e) Analysis on Proanthocyanidin Components

The obtained seed extract, hydrothermally seed extract, partitioned concentrate of seed extract, and partitioned of concentrate of hydrothermally-treated seed extract were each analyzed by high performance liquid chromatography (HPLC) (Prominence HPLC+fluorescence detector: RF-10AXL manufactured by Shimazu Corp.). As controls, a skin extract and an extract obtained by drying the water phase obtained at the above partition step d) were also analyzed in the same manner. Table 1 and FIG. 2 show the results.

HPLC measurement conditions are as follows: Column Inertsil ODS-3 (250×4.6 mm): mobile phase A (0.5% trifluoroacetic acid in water), mobile phase B (0.5% trifluoroacetic acid in methanol), gradient: 0 to 5 min (A/B=90/10), 5 to 15 min (A/B=10/90-25/75), 15 to 35 min (A/B=25/75-35/65); flow rate 1.0 mL/min; and detection method UV (280 & 520 nm).

TABLE 1

Proanthocyanidin-containing extracts and contents of proanthocyanidins contained in them (g/100 g of composition)

| Extracts | Procyanidin (PC) | | Propelargonidin (PP) | | Total quantity of proantho-cyanidins |
|---|---|---|---|---|---|
| | Dimer | Trimer | Dimer | Trimer | |
| Seed extract | 0.9 | 1.1 | 0.6 | 1.6 | 4.2 |
| Hydrothermally-treated seed extract | 1.3 | 2.0 | 0.8 | 2.4 | 6.5 |
| Partitioned concentrate of seed extract | 2.1 | 2.1 | 1.3 | 3.4 | 8.9 |
| Partitioned concentrate of hydrothermally-treated seed extract | 3.0 | 3.8 | 1.7 | 5.1 | 13.6 |

As shown in FIG. 2, the skin extract did not contain proanthocyanidins. In addition, the extract obtained by drying the water phase of the partition step (d) did not contain proanthocyanidins either. The main component of the extract obtained by drying the water phase was ellagitannins.

Example 2

Evaluation Test-1 of Antihypertensive Effect by Boysenberry Seed Extract

Figure 3:
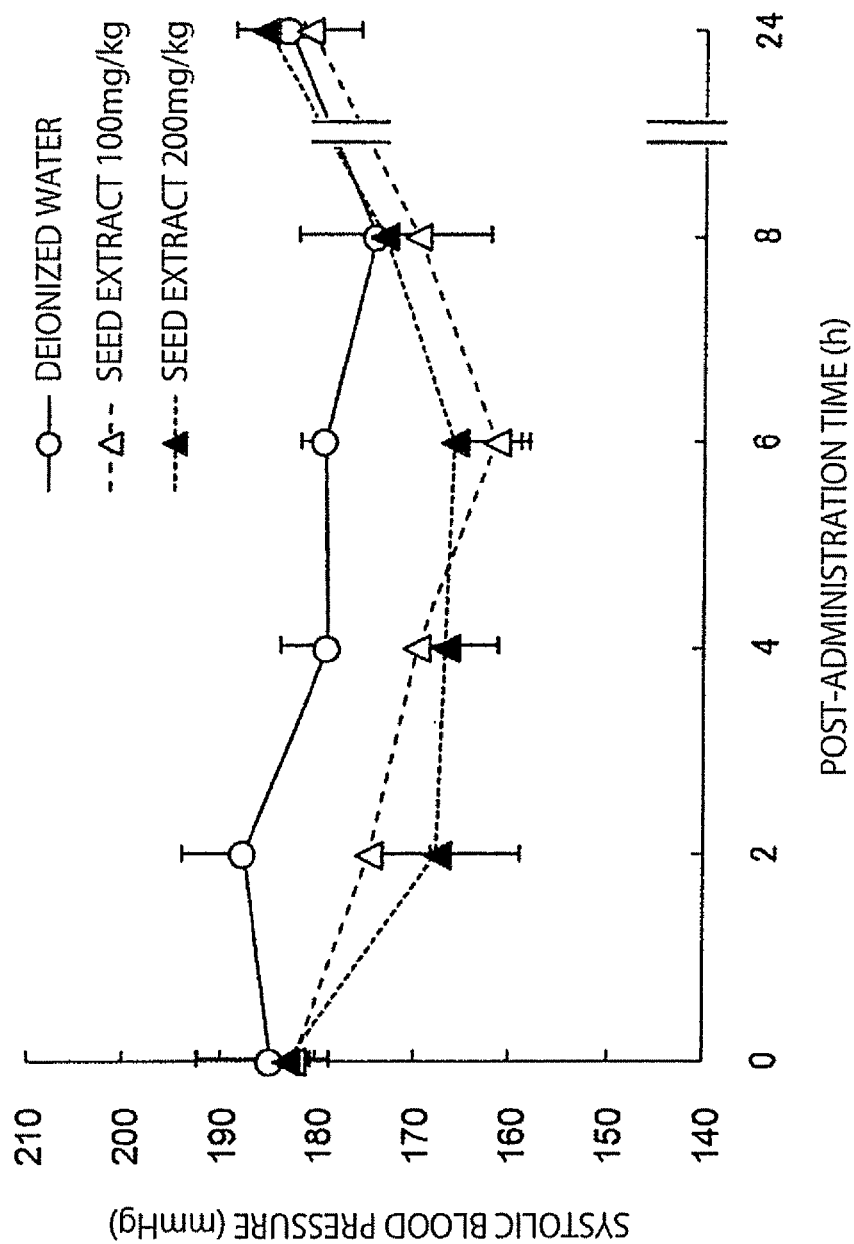
FIG. 3 shows a graph showing results of an evaluation test of antihypertensive effect described in Example 2.

Spontaneously hypertensive rats: SHR/Izm (males, Aged 14 to 15 weeks, and weighing 280 to 310 g, obtained from Japan SLC, Inc.) were divided into three groups (n=5 or 6). After fasting for 15 hours, deionized water was orally administered to one group as a control group. To the remaining two groups as sample administration groups, the seed extract obtained in Example 1 was forcefully orally administered into the stomach using a sonde at a dose of 200 mg/kg or 100 mg/kg of the seed extract in each group, which was set as a high-dose group or a low-dose group. Systolic blood pressures after 2, 4, 6, 8, or 24 hours of the administration were measured three times per rat using a noninvasive automatic blood pressure monitoring system for mice and rats (manufactured by Softron Corp.) by the tail-cuff method. Values of the three-time measurements in each rat were averaged to determine a measurement value. A significance test was performed using the Student's t-test. FIG. 3 shows the results. As shown in FIG. 3, it was observed that the high-dose group exhibited a significant reduction of systolic blood pressure for up to 2 to 6 hours after the administration and the low-dose group exhibited a significant reduction thereof after 6 hours of the administration, as compared to the control group.

Example 3

Evaluation Test-2 of Antihypertensive Effect by Boysenberry Seed Extract

Figure 4:
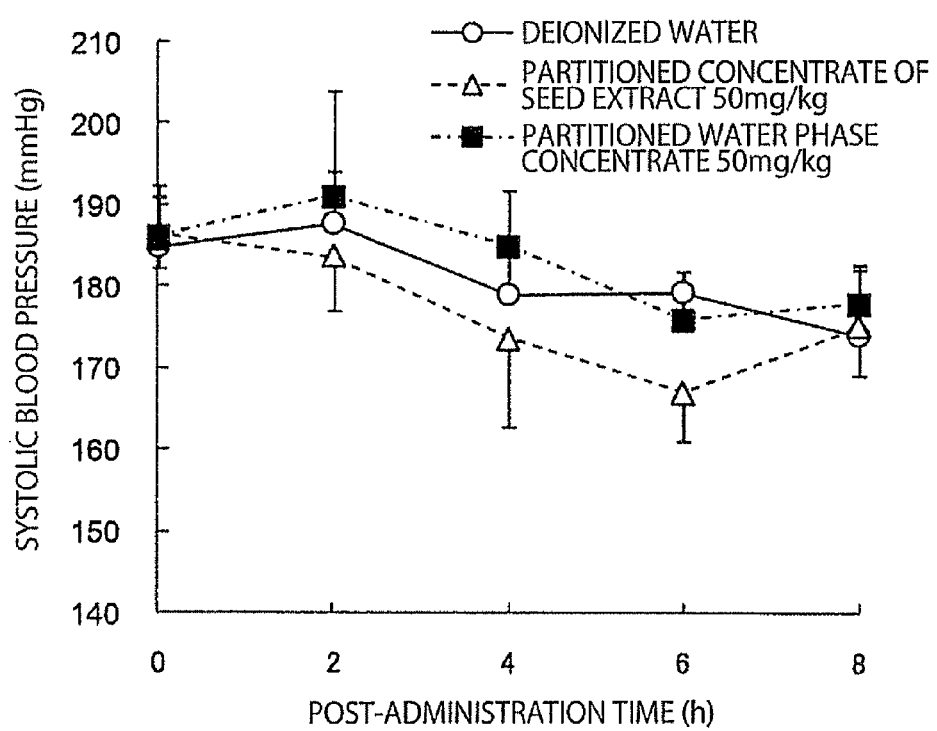
FIG. 4 shows a graph showing results of an evaluation test of antihypertensive effect described in Example 3.

Spontaneously hypertensive rats: SHR/Izm (males, aged 14 to 15 weeks, and weighing 280 to 310 g) were divided into three groups (n=6). After fasting for 15 hours, deionized water was orally administered to one group as a control group. Another one group as a partitioned concentrate of seed extract (ethyl acetate phase) administration group was orally administered 50 mg/kg of the partitioned concentrate of seed extract obtained in Example 1 and a remaining one group as a partitioned water phase concentrate administration group was forcefully orally administered 50 mg/kg of the extract obtained by drying the water phase at the partition step in Example 1. Blood pressures after 2, 4, 6, or 8 hours from the administration were measured in the same manner as Example 2 to obtain the results shown in FIG. 4. The partitioned concentrate of seed extract (ethyl acetate phase) administration group exhibited a significant reduction of systolic blood pressure after 6 hours of the administration as compared to the control group. However, no significant reduction of systolic blood pressure was observed in the partitioned water phase concentrate administration group.

Example 4

Oral Absorbability Evaluation Test of Proanthocyanidins Extracted from Boysenberry Seed The test animal used was Wistar rats (males, aged 9 weeks, with initial weight of 190 to 210 g, obtained from Japan SLC, Inc.). After fasting for 12 hours, the Wister rats were forcefully orally administered each 1000 mg/kg of the partitioned concentrate of seed extract or the partitioned concentrate of thermally-treated seed extract obtained in Example 1. Then, every 1, 2, 4, and 6 hours after the administration, the rats were killed to collect the whole blood. Each whole blood was centrifuged for 10 minutes at 4° C. at 2,000×g to obtain blood plasma as a supernatant. To 1 mL of each blood plasma were added 30 µL of 50% formic acid and 100 µL of 10 mM ascorbic acid solution to mix together, and to 1 mL of the mixed blood plasma solution were added 50 µL of (1 µg of) a catechol solution as an internal standard reagent and 30 µL of phosphoric acid to prepare each sample for analysis. Regarding the samples, measurements of a procyanidin dimer, a propelargonidin dimer, a procyanidin trimer, and a propelargonidin trimer were carried out at molecular weights of 577/289, 561/289, 865/289, and 849/289, using a liquid chromatography-mass spectrometry (LC/MS) (Shimadzu Prominence UFLC manufactured by Shimadzu Corp.; with ODS column; gradient elution with formic acid, methanol, and water) and MS/MS (API 3200 manufactured by Applied Biosystems Co. Ltd., negative-ion mode) to determine the quantities of the proanthocyanidins in the blood plasma. Table 2 shows the results.

Figure 5:
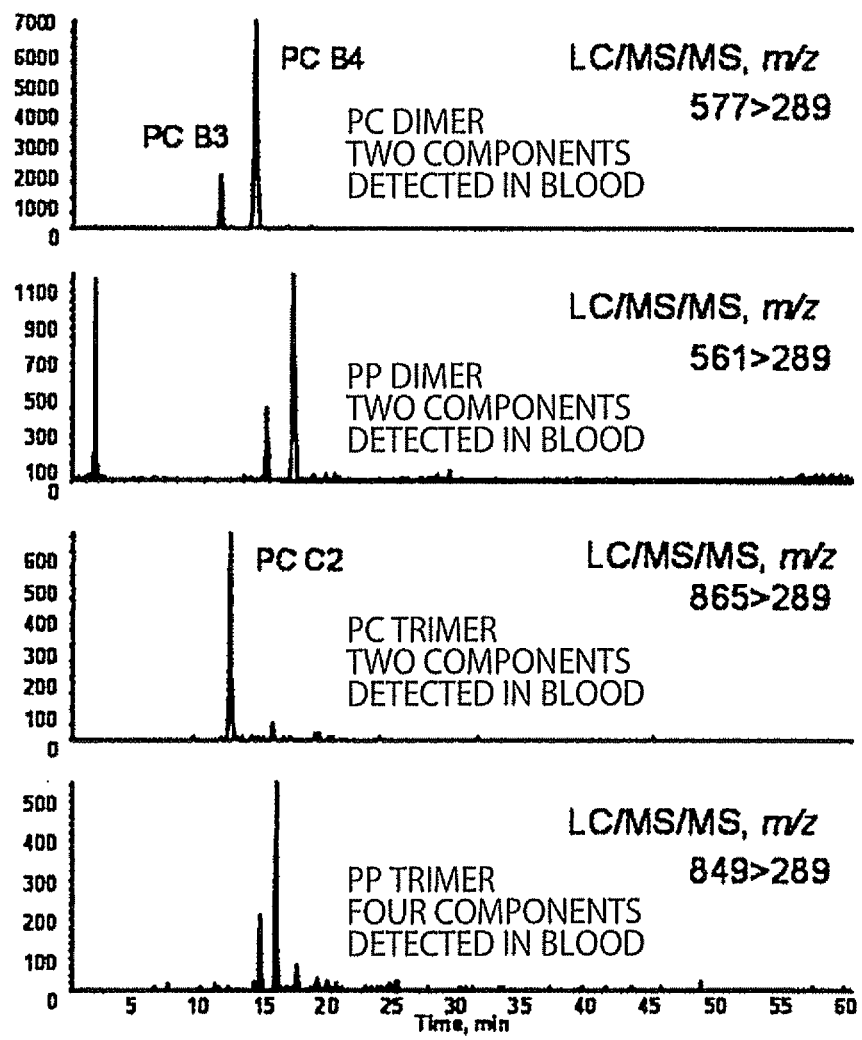
FIG. 5 shows data showing results of LC/MS/MS analysis on blood components indicating that proanthocyanidin dimers and trimers contained in a Boysenberry seed extract described in Example 4 were orally absorbed.

Additionally, FIG. 5 and Table 3 show LC/MS charts of the measurements of proanthocyanidin dimer and trimer components in the blood plasma after 2 hours of the administration of the partitioned concentrate of seed extract.

proanthocyanidin equivalent quantities of the administered extracts and blood concentrations of the proanthocyanidins.

Example 5

Comparison of Vasorelaxant Effect Between Boysenberry Seed Extract and Juice Extract (1) Preparation of Sample Solutions
Boysenberry Seed Extract
According to the method for producing a Boysenberry seed extract in Example 1, a Boysenberry seed extract was produced, and the obtained extract (content of proanthocyanidins: 4.3%) was dissolved in deionized water to prepare a Boysenberry seed extract solution (10 mg/mL).
Boysenberry Juice Extract
A solution prepared by dilution with deionized water (400 mL) of 100 mL of a Boysenberry juice concentrate (obtained from Berry Fruit Export NZ) obtained by squeezing and concentrating Boysenberry fruit was loaded on the polyphenol-adsorbing resin column (Amberlite XAD-7HP, 4L, manufactured by Organo Corp.) to wash with deionized water

TABLE 2

Administered Extracts and Blood Plasma Concentrations of Proanthocyanidin Components (Maximum Absorption Concentrations)

| Extract | Administered extracts 1000 mg/kg Proanthocyanidin equivalent mg/kg | Blood plasma concentrations (post-administration time), µg/mL | | | | Total proanthocyanidins concentration |
|---|---|---|---|---|---|---|
| | | Procyanidin | | Propelargonidin | | |
| | | Dimer | Trimer | Dimer | Trimer | |
| Seed extract | 42 | 0.30 (1) | 0.05 (1) | 0.14 (2) | Minute quantity | 0.42 (1) |
| Partitioned concentrate of seed extract | 89 | 0.67 (2) | 0.22 (2) | 0.14 (2) | 0.13 (2) | 1.16 (2) |

TABLE 3

| Composition | | Administration | Blood concentration | B/A |
|---|---|---|---|---|
| Origin (source) | Component | quantity A (mg/kg) | after 2 hours B (µg/mL) | ($\times 10^{-6}$) (kg/ml) |
| Boysenberry seed (present invention) | Total quantity | 89 | 1.16 | 13.3 |
| | PC dimer B3 | 4 | 0.12 | 30.0 |
| | PC dimer B4 | 17 | 0.56 | 32.9 |
| | PC trimer C1 | 8 | 0.20 | 25.0 |
| | PP dimer 1 | 3 | 0.05 | 16.7 |
| | PP trimer 1 | 7 | 0.07 | 10.0 |
| Apple (J. Agri. c Food Chem., 54, 884-892, 2006) | Total quantity | 756 | 10.2 | 13.5 |
| | PC dimer B1 | 50 | 0.12 | 2.4 |
| | PC dimer B2 | 91 | 0.23 | 2.5 |
| | PC trimer C1 | 63 | 0.12 | 1.9 |
| Grape seed (Br J Nutr., 103, 944-952, 2010) | PC dimer mix | 250 (µmol/kg) | 0.0013 (n mol/mL) | 0.005 |

As shown in Tables 2 and 3 and FIG. 5, it was observed that proanthocyanidin dimers and trimers contained in the administered extracts were all orally absorbed and transferred into the blood. Additionally, there was a high correlation between equivalent to a column volume. Then, the adsorption column was eluted with an amount of ethanol that is two times the column volume. The obtained elution solution was concentrated, and then, freeze-dried to obtain Boysenberry juice extract powder (4.40 g) (content of proanthocyanidins: 0.13%). The powder was dissolved into deionized water to prepare a Boysenberry juice extract solution (10 mg/mL).

(2) Measurement of Vasorelaxation

Figure 6:
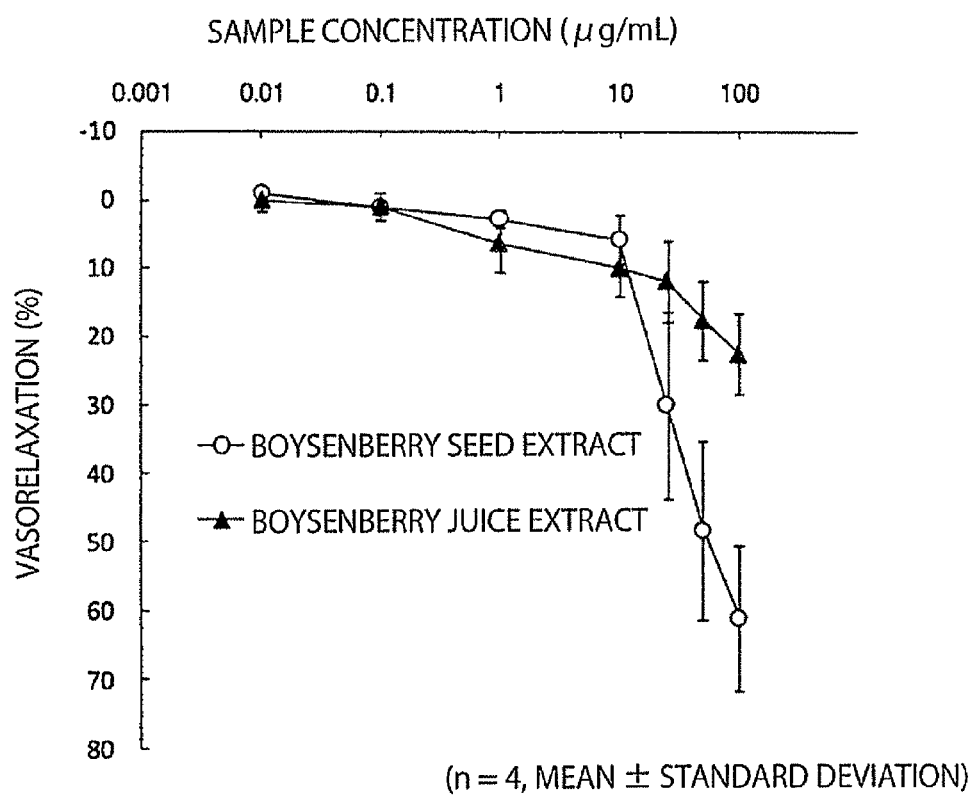
FIG. 6 shows a graph showing vasorelaxant effects in vitro of a Boysenberry seed extract and a Boysenberry juice extract described in Example 5.

Thoracic aortas of Wistar rats of 8 to 11 weeks old were cut into 2- to 3-mm segments, which were mounted on a Magnus experimental device (AP-5 model manufactured by Iwashiya Kishimoto Medical Instruments Co. Ltd.) filled with 20 mL of a phosphate buffer solution to apply a tension of 300 mg. When baseline tension stabilized after equilibration, 0.2 mL of 10 µM norepinephrine (NE) as a contractile agent was added (NE final concentration: 0.1 µM). After tension increased up to approximately 3000 mg and became constant, each sample solution was added such that an initial concentration in an organ bath became 0.01 µg/mL, and next, the each sample solution was accumulatingly added such that the concentration in the organ bath became 0.1, 1, 10, 30, 60 µg/mL, and finally the final concentration became 100 µg/mL. The quantity of tension reduced due to sample addition was shown by mean value±standard deviation (n=4), in which vasorelaxation was estimated in percentage that regarded a value at non-addition of each sample as 100. FIG. 6 shows the results.

Example 6

Comparison of Proanthocyanidin Components and Polyphenol Components Between Boysenberry Seed Extract and Juice Extract (1) Preparation of Sample Solutions The Boysenberry seed extract obtained in Example 1 and the juice extract (content of proanthocyanidins: 0.13%) produced according to the method for producing a Boysenberry juice extract in Example 5 were dissolved in methanol (1 mg/mL) to obtain a seed extract solution and a juice extract solution.

(2) Analysis on Proanthocyanidin Components

The Boysenberry seed extract solution and the Boysenberry juice extract solution dissolved in methanol were analyzed according to the method described in the (e) Analysis on Proanthocyanidin Components in Example 1. Table 4 shows the results.

TABLE 4

Contents of proanthocyanidin components contained in Boysenberry seed extract and juice extract (g/100 g of composition)

| Extract | Procyanidin (PC) | | Propelargonidin (PP) | | Total quantity of proanthocyanidins |
|---|---|---|---|---|---|
| | Dimer | Trimer | Dimer | Trimer | |
| Seed extract | 0.9 | 1.1 | 0.6 | 1.6 | 4.2 |
| Juice extract | 0.11 | 0.01 | 0.01 | 0 | 0.13 |

(3) Comparison of Polyphenol Components

A Boysenberry seed extract was produced according to Example 1, except that, at the step (c) of the method for producing a Boysenberry seed extract in Example 1, the polyphenols adsorbed to the absorbent column were eluted with 60% ethanol two times the column volume, and then, also eluted with 60% acetone solution, but freeze-drying was not carried out. Additionally, a Boysenberry juice extract was produced according to Example 5, except that, in the method for producing a Boysenberry juice extract in Example 5, the polyphenols adsorbed to the absorbent column were eluted with 60% ethanol two times the column volume, and then, also eluted with 60% acetone solution, but freeze-drying was not carried out. The seed extract and the juice extract were dissolved in methanol (1 mg/mL) to obtain a seed extract solution and a juice extract solution.

According to the above (2), analysis on polyphenol components was conducted. Table 5 shows the results. In addition, from a ratio between terminal units and extension units, a mean degree of polymerization of the proanthocyanidins was also measured.

TABLE 5

Components and contents of polyphenols contained in Boysenberry seed extract and juice extract [EC: epicatechin, CA: catechin, (E)CA: catechin or epicatechin, (E)AF: afzelechin or epiafzelechin] (The content values are the mean of three replicates; (standard deviation < ±15%)

| Components | Structures | Contents (mg) | |
|---|---|---|---|
| | | Seed extract (100 g) | Juice extract (100 ml) |
| Proanthocyanidins | | 4.22 | 0.13 |
| Procyanidin B3 | CA → CA | 0.19 | 0.04 |
| Procyanidin B4 | CA → EC | 0.74 | 0.07 |
| Procyanidin C2 | CA → CA → CA | 0.41 | 0.01 |
| Procyanidin trimer | (E)AF → (E)AF → (E)CA | 0.66 | — |
| Propelargonidin dimer | (E)AF → (E)CA | 0.14 | — |
| Propelargonidin dimer | (E)AF → (E)CA | 0.44 | 0.01 |
| Propelargonidin trimer | (E)AF → (E)AF → (E)CA | 0.21 | — |
| Propelargonidin trimer | (E)AF → (E)AF → (E)CA | 0.26 | — |
| Propelargonidin trimer | (E)AF → (E)AF → (E)CA | 0.24 | — |
| Propelargonidin trimer | (E)CA → (E)AF → (E)CA | 0.44 | — |
| Propelargonidin trimer | (E)AF → (E)CA → (E)CA | 0.17 | — |
| Propelargonidin trimer | (E)AF → (E)CA → (E)CA | 0.31 | — |
| Ellagitannins | | 50.43 | 13.19 |
| Anthocyanins | | 1.85 | 11.88 |
| Ellagic acid | | 2.11 | 0.74 |
| Flavanol monomer | | 0.71 | 0.22 |
| Flavonols | | 1.43 | 0.37 |

As shown in Table 5, the content of the proanthocyanidins contained in the Boysenberry seed extract was 4.22 mg/100 g and the components thereof included four kinds of procyanidins and eight kinds of propelargonidins. Meanwhile, the content of the proanthocyanidins contained in the juice extract was 0.13 mg/100 mL and the components thereof included three kinds of procyanidins and one kind of propelargonidin. The mean degree of polymerization of the Boysenberry seed extract was 2.8±0.3 and the mean degree of polymerization of the juice extract was 1.9±0.1 (mean of three replicates).

Example 7

Degree of Polymerization and Vasorelaxant Activity of Procyanidin

Vasorelaxion (%) was measured (n=3 or 4) using five kinds of procyanidins: PC B2 (dimer) (obtained from Extrasynthese Co., Ltd. (Genay Cedex, France)), PC B4 (dimer) (purified by preparative HPLC from Boysenberry seed polyphenol), PC C1 (trimer), PC 4 (tetramer), and PC 5-10 (pentamer to decamer) (purified by preparative HPLC from cacao polyphenol), and epicatechin (monomer) (obtained from Extrasynthese Co., Ltd. (Genay Cedex, France)).

Figure 7:
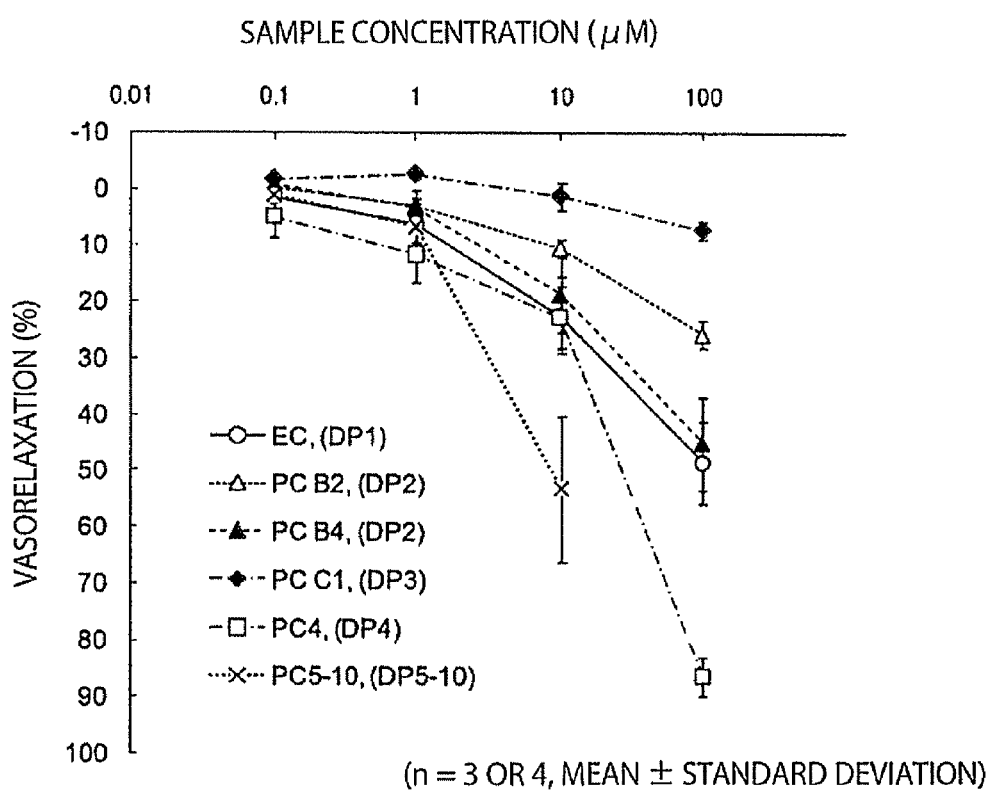
FIG. 7 shows a graph showing the degrees of polymerization and vasorelaxant activities of procyanidins described in Example 7.

Vasorelaxant activity was obtained by measuring vasorelaxation according to the method described in Example 5 (2). FIG. 7 shows the results.

Example 8

A Food and Beverage Product

Candy

To 58 wt % of sucrose, 38 wt % of starch syrup, and 1 wt % of citric acid was added the seed extract obtained in Example 1 such that a blending ratio of the extract was 3 wt % to produce candy having antihypertensive effect. The obtained candy had no problem with taste and like, and was good quality.

Example 9

A Food and Beverage Product

Chewing Gum

To 70.5 wt % of sucrose, 20.0 wt % of gum base, 3.0 wt % of flavoring material, and 1.5 wt % of citric acid was added the partitioned concentrate of seed extract obtained in Example 1 such that a blending ratio of the extract was 5.0 wt % to produce chewing gum having antihypertensive effect. The obtained chewing gum had no problem with taste or like, and was good quality.

Example 10

A Food and Beverage Product

Chocolate

Into chocolate including 60 wt % of a chocolate portion and 40 wt % of a cream portion was added cream to produce chocolate. In the cream portion, respective materials were blended in a ratio of 20 wt % of sugar, 44 wt % of oil and fat, 30 wt % of dried milk, 1 wt % of flavoring material, and 5 wt % of the seed extract obtained in Example 1 to produce chocolate having antihypertensive effect. The obtained chocolate had no problem with taste or the like and was good quality.

Example 11

A Food and Beverage Product

Soft Drink

To 3.0 wt % of isomerized sugar solution, 3.0 wt % of sucrose, 0.1 wt % of concentrated fruit juice, 0.3 wt % of an acidulant, and 0.2 wt % of flavoring material was added the partitioned concentrate of seed extract obtained in Example 1 such that a blending ratio of the extract was 0.1 wt %, and also water was added up to 100 wt % to produce soft drink having antihypertensive effect. The obtained soft drink had no problem with taste or the like and was good quality.

Example 12

Tablet

To 88.5 wt % of crystalline glucose hydrate, 1.0 wt % of sucrose ester, and 0.5 wt % of flavoring material was added the partitioned concentrate of seed extract obtained in Example 1 such that a blending ratio of the extract was 10 wt %, and then, the mixture was molded under pressure to produce tablet having antihypertensive effect.

The invention claimed is:

1. A method for lowering elevated blood pressure in a mammal, comprising:
   administering or feeding to the mammal having elevated blood pressure a composition comprising, as the active ingredient, a Boysenberry seed extract comprising an effective dose of a proanthocyanidin dimer or trimer extracted from Boysenberry seeds,
   wherein the proanthocyanidin dimer or trimer comprises a propelargonidin.

2. The method according to claim 1, wherein the extract is a Boysenberry seed water-soluble organic solvent extract or a Boysenberry seed water-containing organic solvent extract.

3. The method according to claim 1, wherein the extract is a water-soluble organic solvent extract or a water-containing organic solvent extract of Boysenberry seeds that have been subjected to hydrothermal treatment before extraction.

4. The method according to claim 1, wherein the proanthocyanidin dimer or trimer is procyanidin and propelargonidin.

5. The method according to claim 1, wherein the Boysenberry seeds are obtained from a Boysenberry pomace.

6. The method according to claim 1, wherein the composition is a food and beverage product composition.

7. The method according to claim 6, wherein the food and beverage product composition contains 4 wt % or more of the proanthocyanidin dimer or trimer extracted from Boysenberry seeds.

8. The method according to claim 6, wherein the food and beverage product is a health food, a dietary supplement, or a food and beverage product with an indication of reduced disease risk attached thereto.

9. The method according to claim 1, wherein the composition is a pharmaceutical product composition.

10. A method for treating or ameliorating a disease selected from hypertension, circulatory disease, high blood pressure-induced arteriosclerosis, heart disease, cerebral apoplexy, or kidney disease, comprising:
    administering or feeding to a subject having the disease composition comprising, as the active ingredient, a Boysenberry seed extract comprising an effective dose of a proanthocyanidin dimer or trimer extracted from Boysenberry seeds,
    wherein the proanthocyanidin dimer or trimer comprises a propelargonidin.

11. The method according to claim 10, wherein the extract is a Boysenberry seed water-soluble organic solvent extract or a Boysenberry seed water-containing organic solvent extract.

12. The method according to claim 10, wherein the extract is a water-soluble organic solvent extract or a water-containing organic solvent extract of Boysenberry seeds wherein the Boysenberry seeds have been subjected to hydrothermal treatment before extraction.

13. The method according to claim 10, wherein the proanthocyanidin dimer or trimer extracted from Boysenberry seeds is procyanidin and propelargonidin.

14. The method according to claim 10, wherein the Boysenberry seeds are obtained from a Boysenberry pomace.

15. The method according to claim 10, wherein the composition is a food and beverage product composition.

16. The method according to claim 15, wherein the food and beverage product composition contains 4 wt % or more of the proanthocyanidin dimer or trimer extracted from Boysenberry seeds.

17. The method according to claim 15, wherein the food and beverage product is a health food, a dietary supplement, or a food and beverage product with an indication of reduced disease risk attached thereto.

18. The method according to claim 10, wherein the composition is a pharmaceutical product composition.

* * * * *